United States Patent [19]

Oakman

[11] 4,292,837
[45] Oct. 6, 1981

[54] LIQUID TESTING APPARATUS

[75] Inventor: Ronald A. Oakman, Wraysbury, near Staines, England

[73] Assignee: Stanhope-Seta Limited, Egham, England

[21] Appl. No.: 118,323

[22] Filed: Feb. 4, 1980

[30] Foreign Application Priority Data

Feb. 2, 1979 [GB] United Kingdom ............... 03772/79

[51] Int. Cl.³ ............................................. G01N 25/12
[52] U.S. Cl. ............................................. 73/17 R; 73/36
[58] Field of Search ............ 73/17 R, 36, 61 R, 61.2, 73/61.3, 61.4, 38, 35

[56] References Cited

U.S. PATENT DOCUMENTS

| | | | |
|---|---|---|---|
| 2,997,874 | 8/1961 | Billuris et al. | 73/17 |
| 3,070,994 | 1/1963 | Kelley | 73/17 |
| 3,452,586 | 7/1969 | Childs et al. | 73/61 R |

Primary Examiner—Donald O. Woodiel
Attorney, Agent, or Firm—Laubscher, Philpitt & Laubscher

[57] ABSTRACT

Liquid testing apparatus includes a testing cell formed by a vertical bore in a metal block. A flow path for liquid being tested is provided in the cell and the liquid is passed through a restriction, such as a mesh filter, obstruction to flow being measured as the temperature is varied. A preferred use of the apparatus is in testing aviation fuels, when the temperature is gradually lowered. When wax crystals begin to form in the fuel, the impeded flow of fuel through the mesh will indicate this change of state, and this temperature will be the minimum usable temperature of the fuel.

9 Claims, 2 Drawing Figures

LIQUID TESTING APPARATUS

BRIEF DESCRIPTION OF THE PRIOR ART

This invention relates to liquid testing apparatus of the kind in which a characteristic of the liquid is determined.

One example of a use for such apparatus arises in connection with measuring particular properties of aviation fuel. Fuel of this type contains a certain proportion of wax which crystallizes out at a temperature considerably below normal ambient temperature, this crystallization temperature being dependent on a number of factors, one of which is the particular proportion of wax in the fuel. It is necessary to determine this temperature in order to find whether the fuel meets certain prescribed standards.

A known method of determining the wax crystallization temperature is laid down in the joint specification IP16-ASTM D 2386 of the Institute of Petroleum and the American Society for Testing and Materials. This involves visual monitoring of a fuel sample as the temperature is steadily lowered. Crystallization of the wax is seen as a precipitation in the previously clear liquid.

A problem with this known testing method is that a degree of subjectivity is introduced as a result of the visual inspection, and therefore the accuracy of the determination is dependent on the skill of the tester.

SUMMARY OF THE INVENTION

It is an object of the present invention to provide improved liquid testing apparatus which removes the subjective aspect in the determination of a characteristic of the liquid being tested.

Apparatus according to the invention enables liquid being tested to be passed through a restriction, such as a mesh filter, and measuring the obstruction to flow through the restriction as the temperature is varied. A change in the physical state of the liquid may be detected as a variation in the degree of obstruction to flow. In the above example of testing aviation fuel, the temperature is gradually lowered and when wax crystals begin to form in the fuel sample, the impeded flow of fuel through the restriction will indicate this change of state, and the indicated temperature will be that at which the fuel is no longer suitable for use.

From another aspect the invention provides liquid testing apparatus including a testing cell formed by a vertical bore in a metal block and having disposed therewithin a transparent tubular member depending from a cover member closing the top of the cell, said tubular member having its lower end spaced from the bottom of the cell and covered by a mesh filter, aligned transparent rods passing through said block and arranged so that their inner ends form walls of said cell, means arranged to allow the introduction of a liquid sample into said cell and means for introducing and/or extracting air from the top of the spaces of said cell within and without said tubular member.

BRIEF DESCRIPTION OF THE DRAWING

A liquid testing apparatus embodying the invention will now be described with reference to the accompanying drawings, in which.

DETAILED DESCRIPTION

Figure 1:
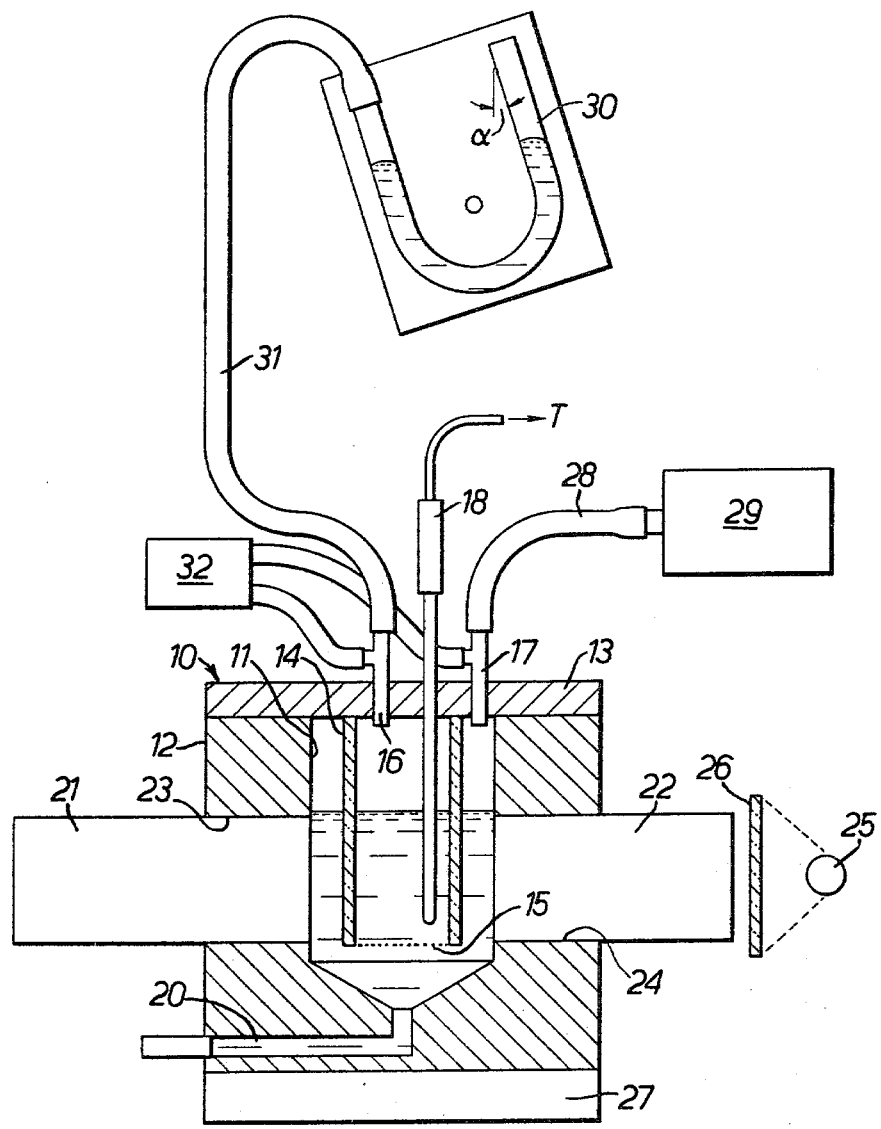
FIG. 1 is a sectional view of the apparatus.

Referring to FIG. 1, there is shown a liquid testing apparatus comprising a testing cell assembly 10 together with ancilliary devices. The cell proper is formed by a cylindrical vertical bore 11 in a metal block 12, conveniently of aluminium. Bore 11 is closed upwardly by a cover plate 13 to which is secured a transparent cylindrical tubular member 14 projecting downwardly from cover plate 13 and concentric with bore 11. The upper end of tubular member 14 is secured in an air-tight manner to cover plate 13 and its lower end is covered by a mesh filter 15, preferably a 400 mesh stainless steel filter. Cover plate 13 is provided with tubulations 16, 17 affording communication from outside the cell to the spaces at the top of the cell within and without the tubular member 14, respectively. A temperature sensor 18 passes through cover plate 13 and provides at T an electrical signal denotive of the temperature of liquid within the cell. At the lowermost point 19 of the cell there is provided a duct 20 through which a sample of liquid to be tested may be introduced into the cell.

Transparent rods 21, 22 are fitted into aligned bores 23, 24 respectively in the cell block 11 and permit optical observation of the interior of the cell, to which end illumination may be provided by a light source 25, light from which is diffused by means of a translucent diffusor plate 26.

The temperature of the cell may be controlled by heating and/or cooling means 27. The device for this purpose may very conveniently be as described hereafter the rate of change of temperature of the liquid under test may be very conveniently controlled as will be described.

The operation of the apparatus is as follows:

Approximately 6 ml of sample is injected into the cell via duct 20 by means of a hypodermic syringe which is left connected. The air displaced from the cell escapes via a drying chamber 29 containing silica gel.

A mercury filled U-tube one end of which is coupled to tubulation 16 by a tube 31 is tilted through a predetermined angle $\alpha$ to provide air pressure to the inner cell. This air pressure displaces the fuel from the inner cell to the outer cell, via filter 15, and is maintained for approximately one second, the pressure is then removed for one second to allow the fuel to refill the inner cell.

A manometer 32 coupled between the tubulations 16 and 17 measures the pressure and vacuum developed across the filter.

When crystals form in the liquid samples as the temperature falls the flow through the filter is impeded and the pressure increases. When the pressure across the filter exceeds 10 mm Hg for one second (1 stroke of pump) this is taken as the lowest temperature at which the fuel ceases to flow. The test cell is then allowed to warm and the temperature at which the flow re-commences can also be noted.

Cooling of the cell assembly is preferably achieved by the combination of compressor refrigeration and thermoelectric cooling as described hereinafter, giving control of temperature from 0° to −70° C.

The test cell being completely sealed prevents the formation of condensation.

The flow rate of 1 ml per second at a pressure of 10 mm Hg via a 400 mesh filter was chosen as tests on fuels of known freezing point by IP16 gave correct results under these conditions. All of these parameters may be changed if necessary to more closely represent actual operating conditions.

A cooling rate of approximately 20°/min near the freezing point is used and a complete test can be completed in 15 minutes.

Figure 2:
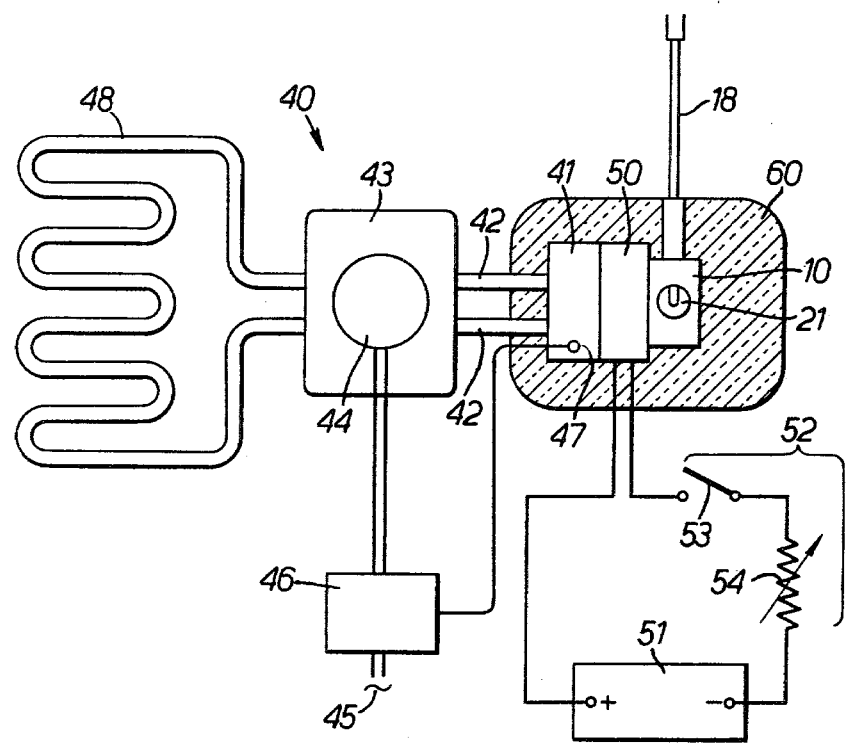
FIG. 2 shows part of apparatus similar to that of FIG. 1, including a temperature controlling means.

FIG. 2 shows in more detail one example of the heating and/or cooling means of FIG. 1.

The apparatus 40 of FIG. 2 includes a reference body, in this case a heat sink, provided by the evaporator block 41 of a refrigerator system. This evaporator, which includes an internal cavity in which a refrigerant liquid is evaporated to produce cooling of the block, is coupled by way of conduits 42 to a compressor and expansion valve assembly 43 including a compressor operated by an electric motor 44 fed from an a.c. power supply 45 by way of a control means 46 responsive to the temperature of evaporator block 41, as sensed by a temperature sensor 47 applied to the evaporator block 41. Assembly 43 is also coupled to a condenser 48 for dissipating heat extracted from evaporator block 41. The arrangement described above operates in well known manner to hold the temperature of evaporator block 41 at a predetermined temperature below ambient, for example −15° C.

The apparatus 40 also includes an observation cell 10 similar to that described above in relation to FIG. 1 which is required to be capable of being taken to a temperature substantially below that of reference body 41, for example, to −50° C. In accordance with the arrangement a Peltier device 50 is interposed between the reference body 41 and cell 10 and is energised from a direct current source 51 to reduce the temperature of cell 10 by the required amount with respect to reference body 41. The current supplied to Peltier device 50, which is a known, commercially available unit, is controlled by appropriate means 52, illustrated as comprising a switch 53 and a variable resistor 54. It is apparent that more complex control means may readily be provided if required, for example, automatic control means to provide a required rate of temperature decrease and/or increase may in known manner respond to temperature-denotive signals developed by a sensor applied to or incorporated in cell 10, conveniently the temperature sensor 18. It is an advantage of the apparatus described that the Peltier device is conveniently operated at a low direct voltage, for example 6 V or 12 V, so that control by known semiconductor switching devices is very simple.

The whole of the cooling means 40, 50, together with cell 10, is enclosed by thermal insulation 60 provided by an envelope of thermal insulating material, conveniently expanded polystyrene, to reduce ingress of heat from the ambience. Rods 21,22 of cell 10 are made of such a length that they extend to the outer surface of thermal insulation 60, so that illumination and viewing of the interior of well 12 is assisted.

An advantage of the apparatus as described is that the transparent rods 21,22 together with the light source 25 and diffusor 26 allow optical observation of the interior of the cell, and therefore the apparatus conforms to the specification IP16.

What is claimed is:

1. Liquid testing apparatus, comprising
   (a) housing means (10) including separable body block and cover plate members (12,13) which cooperate to define a closed testing chamber (11), an inlet (20) for introducing a quantity of the liquid to be tested into said chamber, a vertical tubular divider (14) suspended from said cover member and terminating at its lower end beneath the level of the liquid in the chamber, said divider dividing the upper end of said chamber into concentrically arranged inner and annular outer chamber portions, and an outlet (17) communicating with one of said chamber portions;
   (b) means (30) connected with said housing means for establishing flow of the liquid along a flow path;
   (c) flow restricting means (15) arranged in said flow path;
   (d) detecting means (32) for detecting variations in the resistance to flow of the liquid produced by said flow restricting means; and
   (e) means (18) for indicating the temperature of the liquid.

2. Apparatus as claimed in claim 1, wherein said flow establishing means for causing the liquid to pass through said flow restricting means comprises a device for applying pressure to said liquid.

3. Apparatus as claimed in claim 2, wherein said device for applying pressure comprises a tiltable mercury-containing U-tube having one end thereof connected with said other chamber portion.

4. Apparatus as claimed in claim 1, wherein said flow resistance detecting means comprises a pressure responsive device connected with said flow path between locations upstream and downstream of said flow restricting means, thereby providing an indication of pressure differential means and hence of the flow resistance provided thereby.

5. Apparatus as defined in claim 1, wherein said liquid flow path at least partially includes said tubular divider; and further wherein said flow restricting means comprises a mesh filter attached to said tubular member.

6. Apparatus as defined in claim 5, wherein said divider is formed of transparent material; and further wherein said body block includes transparent means (21,22) defining an optical path including said flow restricting means.

7. Apparatus as defined in claim 6, wherein said transparent means includes a pair of aligned spaced transparent rods (21,22) mounted in said body block on opposite sides of said testing chamber.

8. Liquid testing apparatus including:
   a testing cell comprising a metal block provided with a vertical bore;
   a transparent tubular member disposed in said bore;
   a cover member closing the top of said cell, said transparent tubular member depending from said cover member and having its lower end spaced from the bottom of said cell and covered by a mesh filter;
   aligned transparent rods passing through said block and arranged so that their inner ends form walls of said cell;
   means arranged to allow the introduction of a liquid sample into said cell; and
   means for introducing and/or extracting air from the top of said cell within and without said tubular member.

9. Apparatus as claimed in claim 8, and further including means for controlling the temperature of the liquid sample in said cell.

* * * * *